Figure 1:
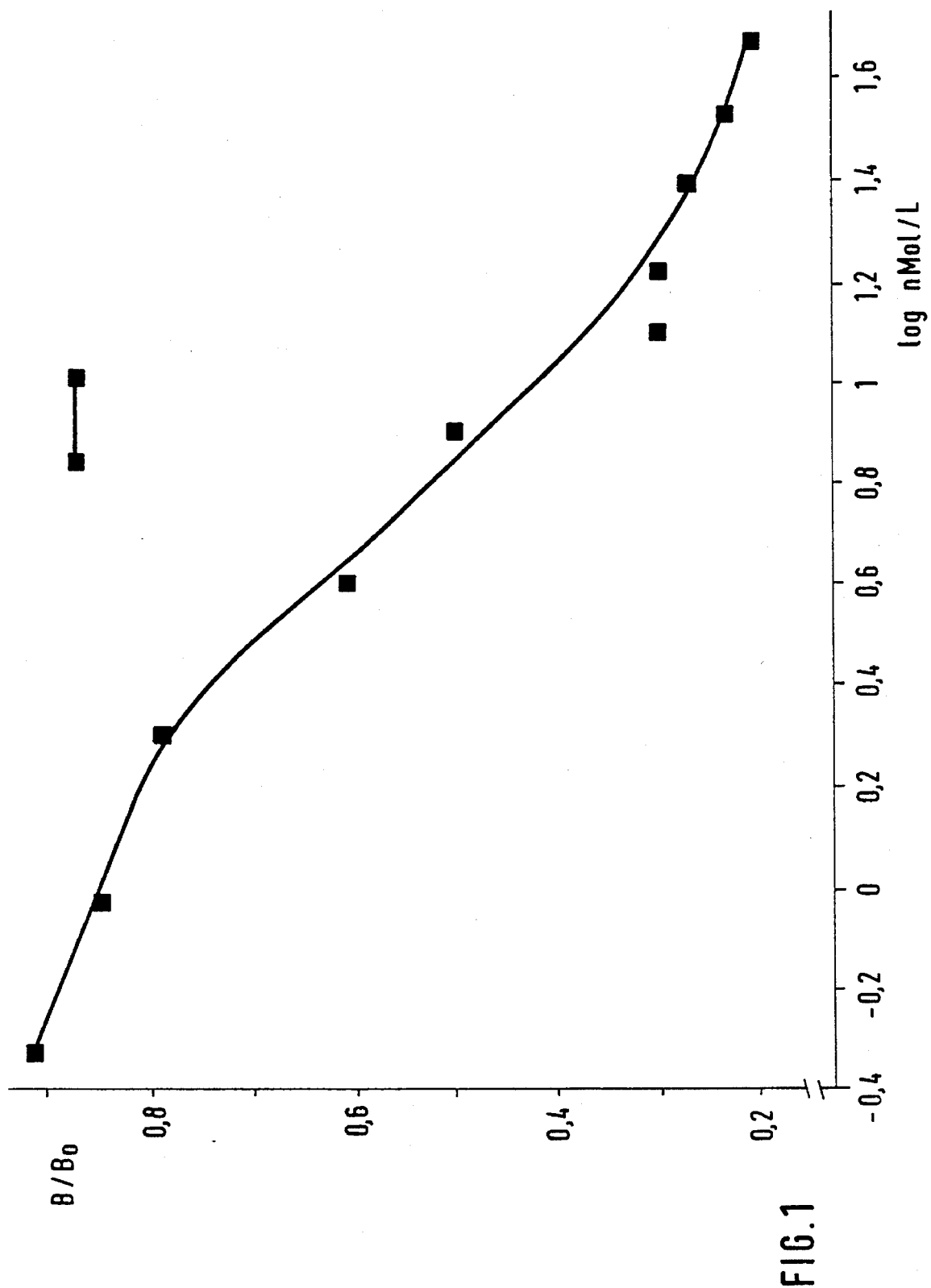

United States Patent [19]

Müllner

[11] Patent Number: 5,514,599
[45] Date of Patent: May 7, 1996

[54] ANTIBODIES AGAINST HIGHLY CONSERVED AMINO ACID SEQUENCES OF INSULIN A PROCESS FOR THE PREPARATION OF THESE ANTIBODIES AND THE USE THEREOF IN IMMUNOASSAYS

[75] Inventor: Stefan Müllner, Frankfurt am Main, Germany

[73] Assignee: Hoechst Aktiengesellschaft, Frankfurt am Main, Germany

[21] Appl. No.: 307,492

[22] Filed: Sep. 16, 1994

Related U.S. Application Data

[63] Continuation of Ser. No. 29,964, Mar. 9, 1993, abandoned, which is a continuation of Ser. No. 586,300, Sep. 21, 1990, abandoned.

[30] Foreign Application Priority Data

Sep. 23, 1989 [DE] Germany .......................... 39 31 787.0
May 30, 1990 [DE] Germany .......................... 40 17 344.5

[51] Int. Cl.⁶ ........................ G01N 33/543; G01N 33/68; G01N 33/74
[52] U.S. Cl. .................. 436/518; 435/7.9; 435/7.92; 435/968; 436/87; 436/811; 436/817; 530/303; 530/387.9
[58] Field of Search .................... 435/7.9, 7.92, 435/968; 436/518, 87, 811, 817; 530/303, 387.9

[56] References Cited

U.S. PATENT DOCUMENTS

| | | | |
|---|---|---|---|
| 4,957,737 | 9/1990 | Heimer et al. | 424/188.1 |
| 4,981,782 | 1/1991 | Judd et al. | 435/5 |
| 5,070,025 | 12/1991 | Klein et al. | 436/546 |

FOREIGN PATENT DOCUMENTS

| | | |
|---|---|---|
| 56126/86 | 10/1986 | Australia . |
| 56803/86 | 4/1987 | Australia . |
| 67132/87 | 7/1987 | Australia . |
| 23679/88 | 4/1989 | Australia . |
| 0314338A1 | 5/1989 | European Pat. Off. . |
| WO 86/01834 | 3/1986 | WIPO . |
| WO 89/00607 | 1/1989 | WIPO . |

OTHER PUBLICATIONS

Kato, K. "Insulin" in Methods of Enzymatic Analysis, Third Edition, 1986.

H. U. Bergmeyer, ed. vol. IX Proteins and peptides pp. 451–462.

Leslie F. Smith, Ph.D. "Amino Acid Sequences of Insulins", Diabetes 21 (Suppl. 2):457–60, 1972.

D. Plachov et al., "The specificity of the interaction between the agretope of an antigen and an Ia–molecule can depend on the T cell clonotype", Biol. Abs. 86(10), No. 103111 (1988).

A. Marks et al., "Characterization of two epitopes on insulin using monoclonal antibodies", Chem. Abs. 102(21):179524y (1985).

Primary Examiner—Toni R. Scheiner
Assistant Examiner—Nancy J. Parsons
Attorney, Agent, or Firm—Finnegan, Henderson, Farabow, Garrett & Dunner

[57] ABSTRACT

Antibodies against highly conserved amino acid sequences of immunogenic substances, a process for the preparation of these antibodies and the use thereof in immunoassays.

The invention relates to antibodies which are obtained by immunization with a peptide fragment which represents a highly conserved amino acid sequence of a native protein. The antibodies according to the invention can be used for the preparation of immunoassays, in particular for the preparation of assays for the determination of genetically engineered products such as insulin which arise as sparingly soluble inclusion bodies in microorganisms. The invention particularly relates to a multispecies insulin assay in the form of an RIA.

13 Claims, 15 Drawing Sheets

ANTIBODIES AGAINST HIGHLY CONSERVED AMINO ACID SEQUENCES OF INSULIN A PROCESS FOR THE PREPARATION OF THESE ANTIBODIES AND THE USE THEREOF IN IMMUNOASSAYS

This is a continuation, of application Ser. No. 08/029,964 filed Mar. 9, 1993, now abandoned; which is a continuation of application Ser. No. 07/586,300 filed Sep. 21, 1990, abandoned.

DESCRIPTION

Antibodies against highly conserved amino acid sequences of immunogenic substances, a process for the preparation of these antibodies and the use thereof in immunoassays.

It is known that immunometric methods are used on an ever increasing scale for the qualitative and quantitative determination of immunogenic substances such as antigens. These methods are based on the formation of a complex of the immunogenic substance with one or more antibodies, with one of the binding partners being labeled for detection. By this it is possible to determine whether and in what quantity a complex has been formed from the immunogenic substance and one or more antibodies. Significant improvements of the immunometric determination methods were made with the introduction of monoclonal antibodies by Milstein and Köhler, the use of which in immunometric assays is described in detail in German Offenlegungsschrift 3,130,834. Immunometric methods for the determination of insulins of certain species have also been described already (J. Havrankova et al., Journal of Immunoassay, 5 (182), 131–144 (1984)). These antibodies were obtained by immunization with the various insulins as the immunogen. The use of antipeptide antibodies which were obtained by immunization with fragments of the relevant protein (antigen) for the identification of native proteins created further possibilities for improvement with regard to the universality of immunometric determinations. Such antipeptide antibodies are now an important tool in the identification of peptides and therefore gene sequences.

These antibodies are of particular importance also for the determination of substances against which antisera can be generated in the customary way only on a limited scale, if at all, because these, injected as complete proteins, are either already too highly active, e.g. peptide hormones, neuropeptides, or too toxic, e.g. diphtheria toxin, viruses and other microorganisms, in the required concentrations. It has likewise been possible to use such antipeptide antibodies successfully in the development of "Synthetic vaccines" (J. G. Sutcliff et al., Science, vol. 219, 660 (1983)). It seems to be advantageous for the selection of the peptide sequence against which polyclonal or monoclonal antibodies are to be obtained in a way known from the literature that at least one part of this sequence is located—i.e. exposed— on the surface of the native protein and thus contains multiply charged or strongly polar functional groups. However, it is expressly stated in the state of the art in this connection that peptide fragments which represent amino acid sequences highly conserved in evolution are very poor immunogens (see G. Walter, J. Immunol. Med. 88, (1986), 149–161). Amino acid sequences highly conserved in evolution are understood in this connection to be such sequences of a given protein which have changed only slightly or not at all in the course of evolution. Thus, for example, horse and rabbit cytochrome C differ in a few amino acid sequences. However, other sequences of this protein from the two animal species are identical. It has been observed that the immune system of one of the animal species does not form antibodies against these identical regions of the cytochrome C of the other species since this sequence is after all also present in the endogenous cytochrome C. It is regarded to be a rule that the immune response to an antigen improves with the magnitude of the evolutionary distance between the immunizing protein and the relevant endogenous protein.

The invention was thus based on the object of providing antibodies which are capable of forming immune complexes both with a native protein and with derivatives, mutants, denatured products, fragments or (synthetic) precursors.

The object was in particular to provide antibodies which form immune complexes with genetically engineered products of a wide variety of species and the derivatives, denatured precursors and fragments thereof. The genetically engineered proteins, such as insulin, were of particular interest in this connection.

A further object was to develop an immunometric assay which allows measurement of the initial yield of genetically engineered products which arise as sparingly soluble inclusion bodies in microorganisms—which has not to date been possible with immunological assays according to the state of the art—and, at the same time, is capable of measuring the protein concentrations in the individual processing steps using the same assay. The initial yield is understood to be that yield which is effectively present immediately after the fermentation. It is not distorted by losses during sample processing and by processing steps.

Surprisingly it has now been found that antibodies which were obtained by immunization with highly conserved peptide fragments of the relevant native protein achieve the abovementioned object.

The invention thus relates to:

antibodies which are obtained by immunization with a peptide fragment which represents a highly conserved amino acid sequence of a native protein.

The invention in particular relates to those antibodies which are obtained by immunization with highly conserved peptide fragments of insulin.

The invention further relates to a process for the preparation of the abovementioned antibodies and to the use thereof in immunometric assays.

Hereinbefore and hereinafter highly conserved amino acid sequences are understood to be those protein fragments of a given protein which is present in several species— even if more or less slightly modified—which have changed in the course of evolution only insubstantially, where appropriate, if at all. An example which may be mentioned here is the octapeptide (14–21) of the insulin A chain (Tyr-Gln-Leu-Glu-Asn-Tyr-Cys-Asn) which is present without any change in many known insulins such as human, pig, sheep, horse, cattle, chicken, duck, turkey, goose, alligator, rattlesnake, colubrid snake, sei whale, elephant, goat, dog, monkey, sperm whale, fin whale, rat, mouse, hamster and rabbit insulin.

A native protein is understood to be a naturally occurring protein.

Peptide fragments and protein fragments are understood to be parts of a relevant peptide/protein, which are a natural component of this peptide/protein. These fragments are connected amino acids (a so-called amino acid sequence)

which represent a section or a beginning or an end of the peptide/protein.

The preparation of the antibodies according to the invention against highly conserved amino acid sequences of native proteins is best carried out in the following way:

1. Selection of the relevant amino acid sequence according to the following criteria:
   a) The relevant sequence should preferably be exposed, i.e. it should be located on the surface of the native protein, which is preferably the case when the sequence contains multiply charged or strongly polar functional groups or when the secondary structure of the protein contains loops which preferably protrude from the molecule. In most cases this condition is met when, for example, asparagine (Asn), aspartic acid (Asp), proline (Pro), glutamine (Gln), glutamic acid (Glu) and/or glycine (Gly) are multiply present in the sequence concerned.
   b) The number of potential epitopes on the selected peptide fragment is to be as small as possible on the one hand, but, on the other hand, the peptide fragment is to be large enough for an immune response. The selected sequence should not exceed 20, preferably 12, particularly preferably 10, very particularly preferably 8 amino acids and should not be shorter than 4, preferably 5, particularly preferably 6 amino acids. Peptide fragments with 6–13, preferably 7–11, in particular 8-10 amino acids have proven suitable.
   c) The selected sequence should preferably not be at the N or C terminus of the relevant native protein, N and C terminus here being understood to be the corresponding termini of the complete native protein. If this complete protein is composed of several proteins which are connected together, the sequence can of course be at an inside N or C terminus of this integrated protein.

2. Preparation of the relevant amino acid sequence

Suitable for the preparation of the selected protein fragment is, for example, the Merrifield peptide synthesis which is known from the literature. However, it is also perfectly possible to obtain suitable fragments from an enzymatic or chemical cleavage of the native protein. Short sequences may also be synthesized in a purely chemical way.

3. Coupling on of a carrier, where necessary

It is advisable to couple a carrier onto the selected protein fragment in particular in the case of short protein fragments which themselves provoke no immune response at all or only an insufficient one, but also in the case of immunogenic fragments. This coupling on takes place by processes known to those skilled in the art, for example via coupling reagents such as glutaraldehyde or N-maleimido-6-caproyl 1-hydroxy-2-nitrobenzene-4-sulfonate sodium salt (mal-sac-HNSA). Examples of carriers which may be used are: polymers such as polyethylene glycol, polyacrylamide or poly-d-glutamine-d-lysine or fatty acid derivatives such as PAM-3-Cys (PAM=palmitoyl) or proteins such as bovine serum albumin (BSA) or keyhole limpet hemocyanin (KLH).

Preferably, several molecules of the protein fragment are coupled to the carrier.

4. Immunization of a species with the protein fragment or with the carrier-bound protein fragment The immunization of a species with the protein fragment or with the carrier-bound protein fragment takes place by processes known from the literature, for example by intramuscular injection of the immunogen, if appropriate together with an adjuvant such as CFA (complete Freund's adjuvant) or IFA (incomplete Freund's adjuvant). If necessary, one or more booster doses can be administered after the immune response has been obtained. The selection of the species is not critical; for example mice, rats, rabbits, sheep or goats are suitable. However, for the preparation of larger amounts of antibody-containing sera it is advantageous to use larger animals, such as sheep or goats.

5. Isolation of the antibodies from the sera

The antiserum can, in principle, be drawn after obtaining the first immune response. However, depending on the animal species used, higher titers are obtained only after one or more booster doses with the relevant immunogen. Depending on the purpose of use, the serum is purified and concentrated or else immediately diluted without further purification in the assay medium and used. The purification and concentration of the serum is particularly advisable for the preparation of sandwich assays. This can, for example, be carried out by ammonium sulfate precipitation and subsequent fractionation on an affinity column on which a relevant antigen has been immobilized. In this process, all proteins which do not show any interaction with the immobilized protein are separated off. The antibodies which recognize the relevant protein—and are thus bound to the immobilized protein—can then be eluted from the column.

As an alternative to the method for obtaining polyclonal antibodies described under 5. above, monoclonal antibodies can of course also be prepared. This is carried out, for example, by immunization of mice, as described under 4. above, and subsequent fusion of the spleen cells of the mice with, for example, NS 1 myeloma cells and cloning of suitable cells. If appropriate, the monoclonal antibodies thus obtained can be multiplied, for example, by injection into nude mice. The preparation of such monoclonal antibodies is in principle known to those skilled in the art and described in the literature. The working up and purification can then be carried out as described under 5. above.

The antibodies according to the invention can be used for the preparation of immunoassays. In such immunoassays, the antibodies according to the invention or an antigen can, for example, be immobilized on a solid phase. Processes for the immobilization of antigens and antibodies on solid phases such as synthetic or natural polymers such as polystyrene, polypropylene, PVC or latex in various geometrical embodiments such as tubes, beads or microtiter plates are known to those skilled in the art. The immunoassay can be, for example, a competitive assay or a sandwich assay. In both cases, one constituent—either the antigen or the antibody—is labeled for detection. Labeling is normally carried out via a radioactive, chemiluminescent or enzymatic label. Processes of these types for labeling antigens and antibodies are also known to those skilled in the art. Since the antibodies according to the invention are capable of recognizing both the native proteins of one species and the corresponding native proteins of other species and even derivatives, fragments, synthetic and natural precursors or denatured products of these proteins— if they contain the peptide fragment which has been used for the immunization or at least subfragments thereof which correspond to at least 60–80% of the peptide fragment which has been used for the immunization— it is advantageous to label the antibodies according to the invention for the preparation of a multi species immunoassay and thus design an RIA (radioimmunoassay), CIA/LIA ((chemi)-luminescence immunoassay) or EIA (enzyme immunoassay) by processes known from the literature.

A buffer system which has proven particularly advantageous for the determination of genetically engineered products, which arise as sparingly soluble inclusion bodies in microorganisms, in an RIA, is one which, in addition to customary buffer systems such as phosphate buffer (Na$_2$HPO$_4$, NaH$_2$PO$_4$), tris buffer (tris(hydroxymethyl)aminomethane) or barbiturate buffer (for example sodium diethylbarbiturate), contains at least one protein such as bovine serum albumin (BSA), lactoalbumin, ovalbumin, egg albumin, skim milk powder or gelatin and at least one ionic detergent such as sodium dodecyl sulfate (SDS), hexadecyltrimethylammonium bromide or a bile salt and/or at least one nonionic detergent such as ®Nonidet P40, ®Triton X100 or ®Tween 20.

In a particular embodiment, the invention relates to antibodies which form immune complexes both with insulins of different species and with insulin derivatives, fragments, synthetic and natural denatured insulin precursors and derivatives of these denatured insulin precursors. For the preparation of these "multispecies insulin antibodies", an insulin fragment is selected as the immunogen according to the abovementioned criteria 1a–b. Suitable examples are the A$_1$–A$_7$ or A$_{11}$–A$_{17}$ or A$_{11}$–A$_{21}$ sequences of the insulin A chain and the regions around the cysteines of the B chain. The insulin A chain (14–21) octapeptide Tyr-Gln-Leu-Glu-Asn-Tyr-Cys-Asn has proven particularly suitable. This octapeptide can be prepared by processes known from the literature (W. K önig, K. Kernebeck, Liebigs Ann. Chem., 1979, 227–247). The coupling on of the carrier, the immunization and the isolation of antibodies is carried out by the process steps 3–5 described above. The insulin antibodies obtained can be used for the preparation of a multispecies insulin assay even without additional processing and purification.

Such a multispecies insulin assay can, for example, be designed as an RIA, CIA/LIA or EIA according to processes known from the literature. The insulin antibodies according to the invention can be present both free in solution (for example in a precipitation RIA) or bound to a solid phase (immobilized). Suitable in the case of the precipitation LIA are, for example, radioactively labeled— preferably with radioiodine—insulins, insulin fragments, insulin derivatives, natural or synthetic insulin precursors or, for example, the radioactively labeled peptide fragment which was used for raising the insulin antibodies according to the invention, in particular the radioiodine-labeled insulin A chain (14–21) octapeptide. For the preparation of a sandwich immunoassay, two antibodies are used, one of which—usually the one not bound to the solid phase—is labeled. The two antibodies may be directed against the same epitope of the insulin, but are preferably directed against differing epitopes of the insulin. For a sandwich immunoassay of this type in which the two antibodies used are directed against different epitopes, polyclonal or monoclonal antibodies which have been affinity purified and labeled with radioiodine are preferably used. The antibodies or antigens (insulin, insulin fragments, insulin derivatives, natural or synthetic precursors) are labeled according to processes known from the literature; the Iodo-Gen Method can, for example, be used for radioiodine labeling.

The multispecies insulin assay according to the invention has the advantage over insulin assays according to the state of the art that it can be used to measure and determine both insulins of various species and insulin derivatives, insulin fragments, synthetic and natural denatured insulin precursors and derivatives of these denatured insulin precursors.

It has been found that even those proteins which contain amino acid sequences representing only 60–80 % of the peptide fragment which was used for the immunization (and hence for raising the antibody) can be detected and determined. Thus, even those proteins which contain only the hexapeptide (16–21) can, for example, be determined in the multispecies insulin assay which contains antibodies obtained by immunization with the insulin A chain (14–21) octapeptide. The following insulins, insulin derivatives or proteins derived from insulin can, for example, be determined in the multispecies insulin assay according to the invention:

1. β-Galactosidase/insulin fusions expressed in *E. coli* P1, P6, P1-trimer-de-Met-de-Cys, P1-trimer-de-Met, P1-poly-Gly-de-Met, P1-poly-Gly-de-Met-de-Cys, P-Lz-gamma;
2. Interleukin-2/insulin fusions expressed in *E. coli* pB40, pK52, pGF12, pIK10, pSW3, pSW2, pSW3*M;
3. trp/insulin fusions expressed in *E. coli* pB70, pINT 14, pINT 30, pINT 41, pSL 27, pINT 91;
4. Insulins from various species Human insulin, pig insulin, sheep insulin, horse insulin, cattle insulin, chicken insulin, duck insulin, turkey insulin, goose insulin, alligator insulin, rattlesnake insulin, colubrid snake insulin, sei whale insulin, elephant insulin, goat insulin, dog insulin, monkey insulin, sperm whale insulin, fin whale insulin, rat insulin, hamster insulin, rabbit insulin;
5. Insulin derivatives B31-mono-Arg-human insulin, B31,B32-di-Arg-human insulin, B1-de-Phe-pig insulin, A14-monoiodo-human insulin;
6. Insulin fragments Insulin A chain tetrasulfonate (bovine), insulin A chain tetrasulfonate (human), insulin A chain (14–21) octapeptide, insulin A chain (16–21) hexapeptide;
7. Insulin precursors Preproinsulin S-sulfonate (P1), preproinsulin (P1), preproinsulin (pSW 3), proinsulin (porcine).

Furthermore, the multispecies insulin assay according to the invention has the advantage that determinations are possible even in the presence of ionic and nonionic detergents, auxiliary proteins, detergent mixtures and detergent/auxiliary protein mixtures. Examples of detergents which can be used are sodium dodecyl sulfate (SDS), ®Triton X 100 or ®Nonidet P 40 and examples of auxiliary proteins are bovine serum albumin (BSA), egg albumin, ovalbumin or *E. coli* proteins. Ionic detergents may preferably be used in the range of 0–0.3%, nonionic detergents preferably in the range of 0–2% and auxiliary proteins preferably in the range of 0–3% (percentages in w/v=weight/volume). Measurement in the presence of these substances has the advantage that even, for example, sparingly soluble products which have been prepared by genetic engineering are accessible to measurement without essentially interfering with the assay, which has not been possible hitherto with immunometric methods according to the state of the art. Neither auxiliary proteins or foreign proteins such as calcitonin or the nonapeptide buserelin nor customary buffer systems essentially interfere with the multispecies assay. Thus, a buffer system which has proven very suitable, for example, for the radioimmunological determination (RIA determination) of genetically engineered products which arise as sparingly soluble inclusion bodies in microorganisms contains, in addition to the customary buffer substances such as phosphate buffer (Na$_2$HPO$_4$, NaH$_2$PO$_4$), tris buffer (tris(hydroxymethyl)aminomethane) or barbiturate buffer (for example sodium diethylbarbiturate), at least one protein such as bovine serum albumin (BSA), lactoalbumin or ovalbumin and at least one ionic detergent such as sodium dodecyl sulfate (SDS), hexadecyltrimethylammonium bromide or a bile salt and/or at least one nonionic detergent such as ®Nonidet P40, ®Triton X100 or ®Tween 20.

Since the insulin antibodies according to the invention can be employed for the equivalent determination of considerably different antigenic insulins, they are also suitable, in combination with previously known highly specific insulin antibodies, for the investigation of the tertiary structure and the location of essential and less essential structural features in the insulin molecule.

EXAMPLES

Example 1

Coupling the insulin A chain (14–21) octapeptide to BSA

The protected insulin A chain (14–21) octapeptide is synthesized by the method of W. König, K. Kernebeck, Liebigs Ann. Chem. 1979, 227–247. For the conjugation to BSA as carrier molecule, the protected insulin A chain (14–21) octapeptide Ddz-Tyr(tBu)-Gln-Leu-Glu(OtBu)-Asn-Tyr(tBu)-Cys(Trt)-AsnOtBu is stripped of all protecting groups by treatment with a mixture of trifluoroacetic acid and ethanethiol (according to W. König, K. Kernebeck, Liebigs Ann. Chem., 1979, 227–247). The resulting product is then covalently bonded to BSA with the aid of the bifunctional coupling reagent N-maleimido-6-caproyl 1-hydroxy-2-nitrobenzene-4-sulfonate sodium salt (mal-sac-HNSA). For this purpose 55 mg of mal-sac-HNSA are added to a solution of 111 mg of BSA (corresponds to 95 equivalents of lysine) in 10 ml of 0.1 molar phosphate buffer at pH 7.4. After stirring at room temperature for 60 minutes, the reaction mixture is chromatographed in 0.1 molar phosphate buffer at pH 6.2 on Sephadex G 25 and the peak which elutes first is collected. 67 mg (65 µmol) of insulin A chain (14–21) octapeptide are added to this solution. The mixture is then left to stand at room temperature overnight. The reaction mixture is now dialyzed against water and the resulting solution is freeze dried.

Yield: 122 mg Protein content: 83%

15 molecules of octapeptide per molecule of BSA (determined by amino acid analysis)

Example 2

Immunization

Three animal species were used for the immunization, namely cross-bred domestic rabbits (number of individuals= 3) and one sheep and one goat. The immunization was started at the same time for all the animals, administering 0.1 mg of the octapeptide/BSA conjugate from Example 1 in CFA (complete Freund's adjuvant, Difco) to each rabbit and 2.5 mg each of the octapeptide/BSA conjugate in CFA to the sheep and the goat intramuscularly as initial dose. In the third week after the initial administration, the animals received booster doses of the same amount of octapeptide/ BSA conjugate in IFA (incomplete Freund's adjuvant, Behring) and this process was repeated in weeks 4, 8, 13, 18 and 25. In weeks 27, 32 and 37, booster doses of the same amount of pure non-BSA-conjugated octapeptide in IFA were administered. The antisera were drawn in week 10 for the first time in each case and then ten days after each booster dose. The titers were determined as described in the literature (T. Chard, "An introduction to Radioimmunoassay and Related Techniques", Elsevier Science Publishers, Amsterdam (1987), pp. 101–102). For this, serial dilution (1:10–1:10$^6$) of the drawn serum in MSTB buffer (for composition of the buffer, see Example 3) was carried out, and the amount of bound tracer in each case was determined under assay conditions (see Example 3). The titer then is that value at which the antibodies of the particular serum with a given dilution bind 50% of the tracer employed. The titer is reported as the reciprocal. The sera of the immunized animals described above had titers of 1:500–1:10,000.

Example 3

Preparing and carrying out a radioimmunoassay
Materials used
Antiserum

For the preparation of a radioimmunoassay, a sheep antiserum (S 239) with a titer of 1:500 was used. The employed antiserum was used directly without further purification. The dilution of the serum was 1:20 (in MSTB buffer); it was stored at −20° C. The dilution for use was 1:500 (in MSTB buffer).

MSTB buffer

The MSTB buffer used was composed of:

0.1M morpholinopropanesulfonic acid (MOPS) adjusted to pH 7.5 with 1M NaOH 2.5% (w/v) bovine serum albumin 0.2% (w/v) sodium dodecyl sulfate 0.2% (w/v) ®Triton X-100

0.04% (w/v) sodium azide

Immunoglobulin solution

An immunoglobulin solution with a concentration of 10 mg/ml of double distilled water was used for carrying out the assay.

Tracer $^{125}$I-labeled pig insulin (Behringwerke AG, Marburg, prod. no. OCSM) was used as tracer (10 ng<74 KBq lyophilisate).

A total activity of 20,000–30,000 counts was used per test tube.

Standards

The protein contents of the standards were determined first. Then the content of substance to be determined later in the RIA (insulins of various species, 16 insulin derivatives, insulin precursors etc.) was determined.

The standards were then adjusted to a concentration of 2,000 ng/ml in MSTB buffer. For recording the standard plots, a geometric dilution series with the following concentrations (data in ng/ml of MSTB buffer) was prepared in each case: 3.71; 7.5; 15; 30; 60; 120; 240; 480; 960; 1,920.
Recording the standard plots (assay conditions)

For the determination of the standard plots, 100 µl of standard, 100 µl of tracer and 100 µl of antiserum were pipetted into each tube (from Sarstedt, order no. 55–535). The sample was mixed well and left to stand at room temperature (18°–25° C.) overnight (18 hours). Before precipitation with 1,000 µl of polyethylene glycol (molecular weight about 4,000), 50 µl of immunoglobulin solution were added and the mixture was mixed well. After 20 minutes, centrifugation at 1,500× g was carried out and the supernatant was decanted off. The precipitate was then measured in a gamma counter (gamma counter 1277, Pharmacia LKB) for 1 minute. Duplicate determinations were used for the evaluation in each case.

Determining the blank

The procedure as described under "Recording the standard plots" above was used for determining the blank. However, 100 µl of MSTB buffer were used here instead of the standard.

Example 4

Measurement of various insulins and proteins derived therefrom in the RIA

Figure 2:
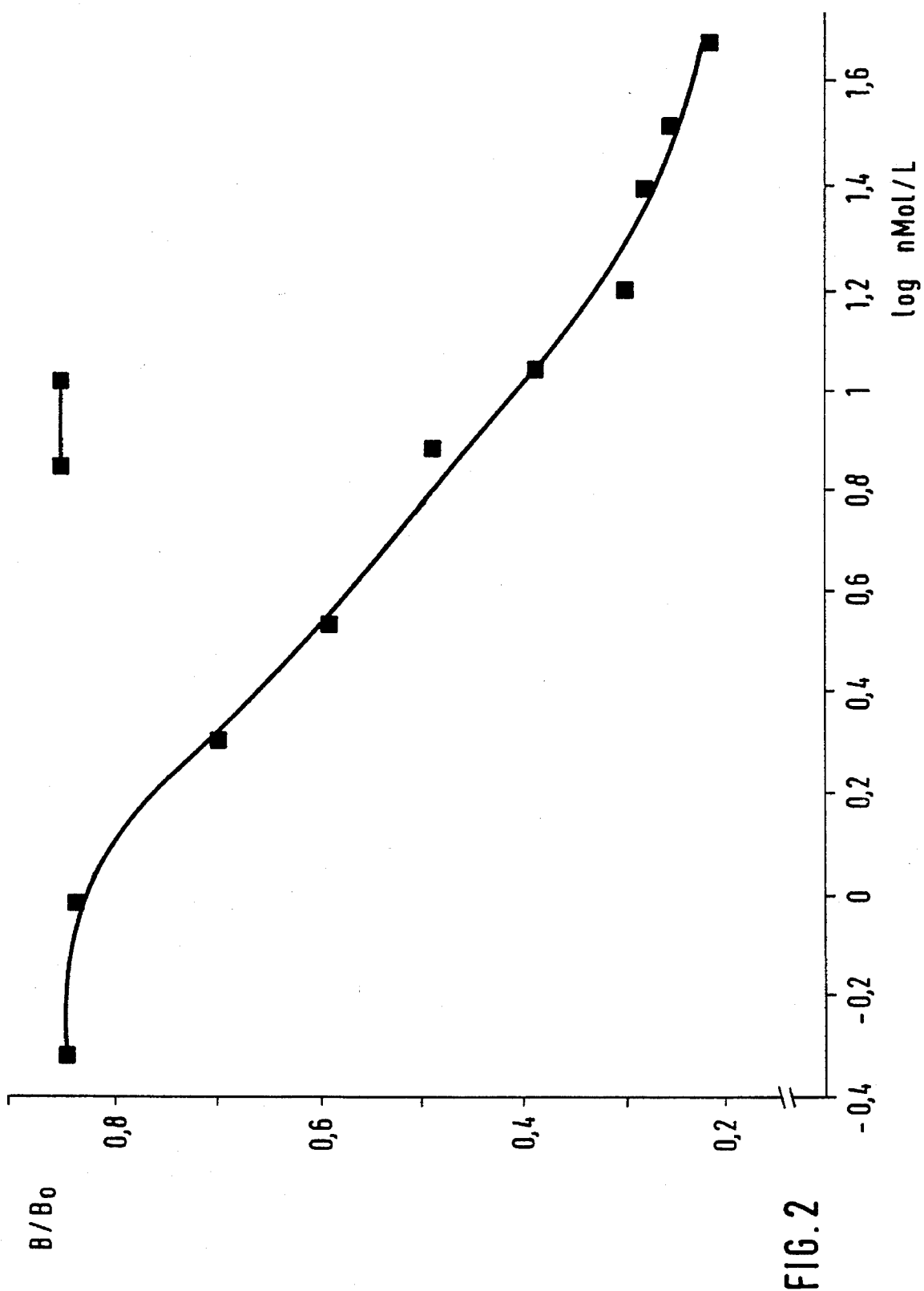
Figure 3:
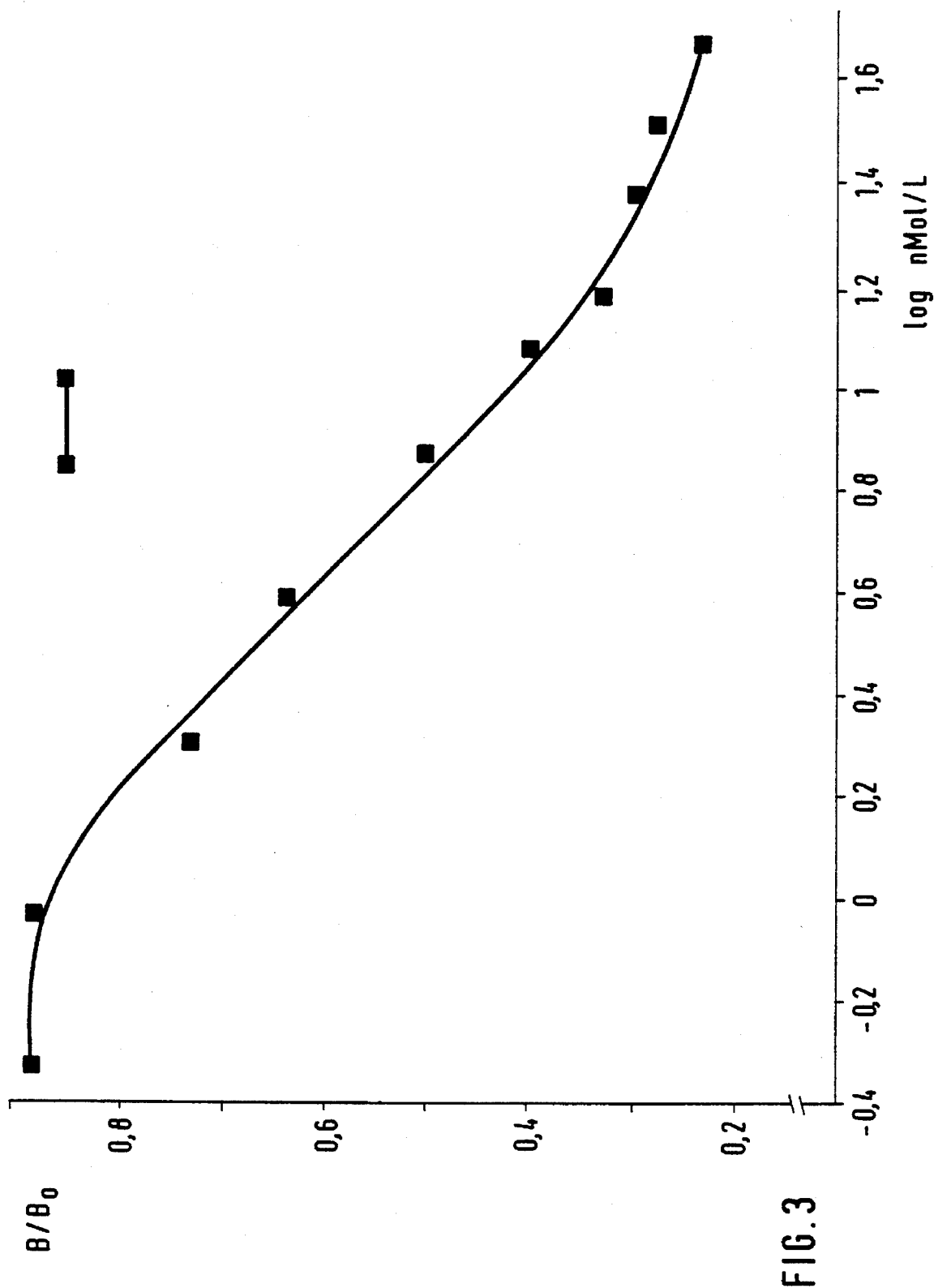
Figure 4:
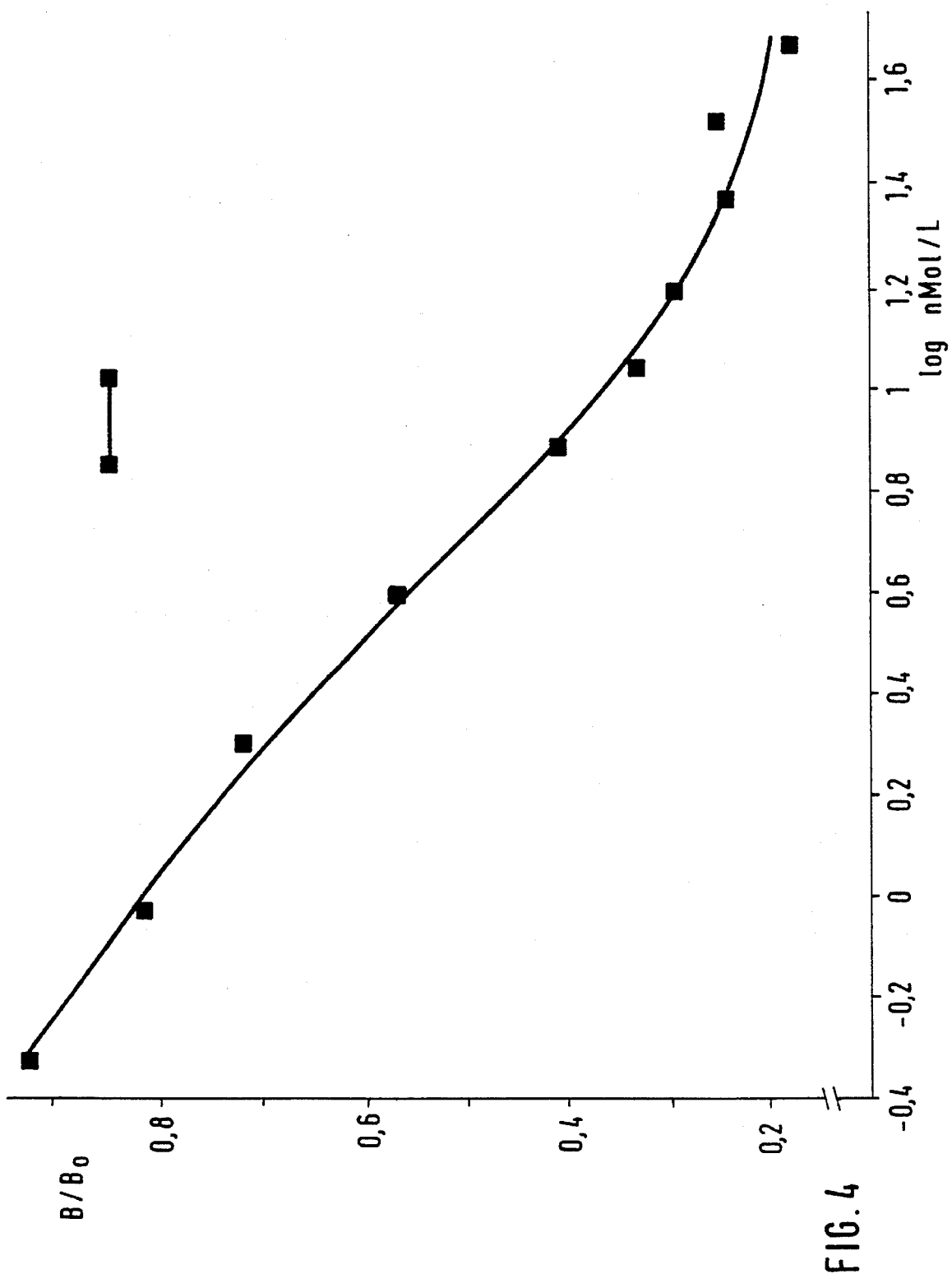
Figure 5:
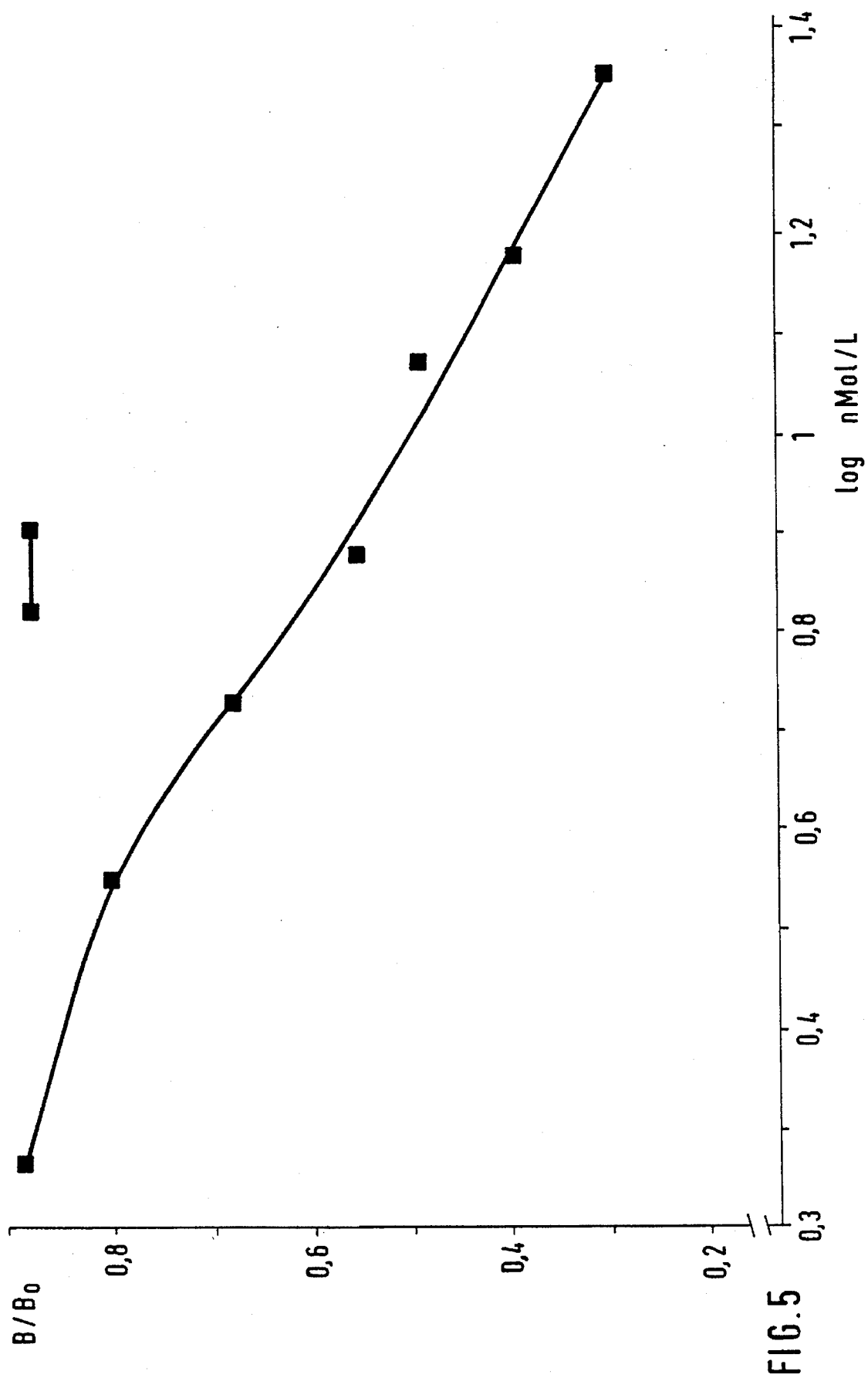
Figure 6:
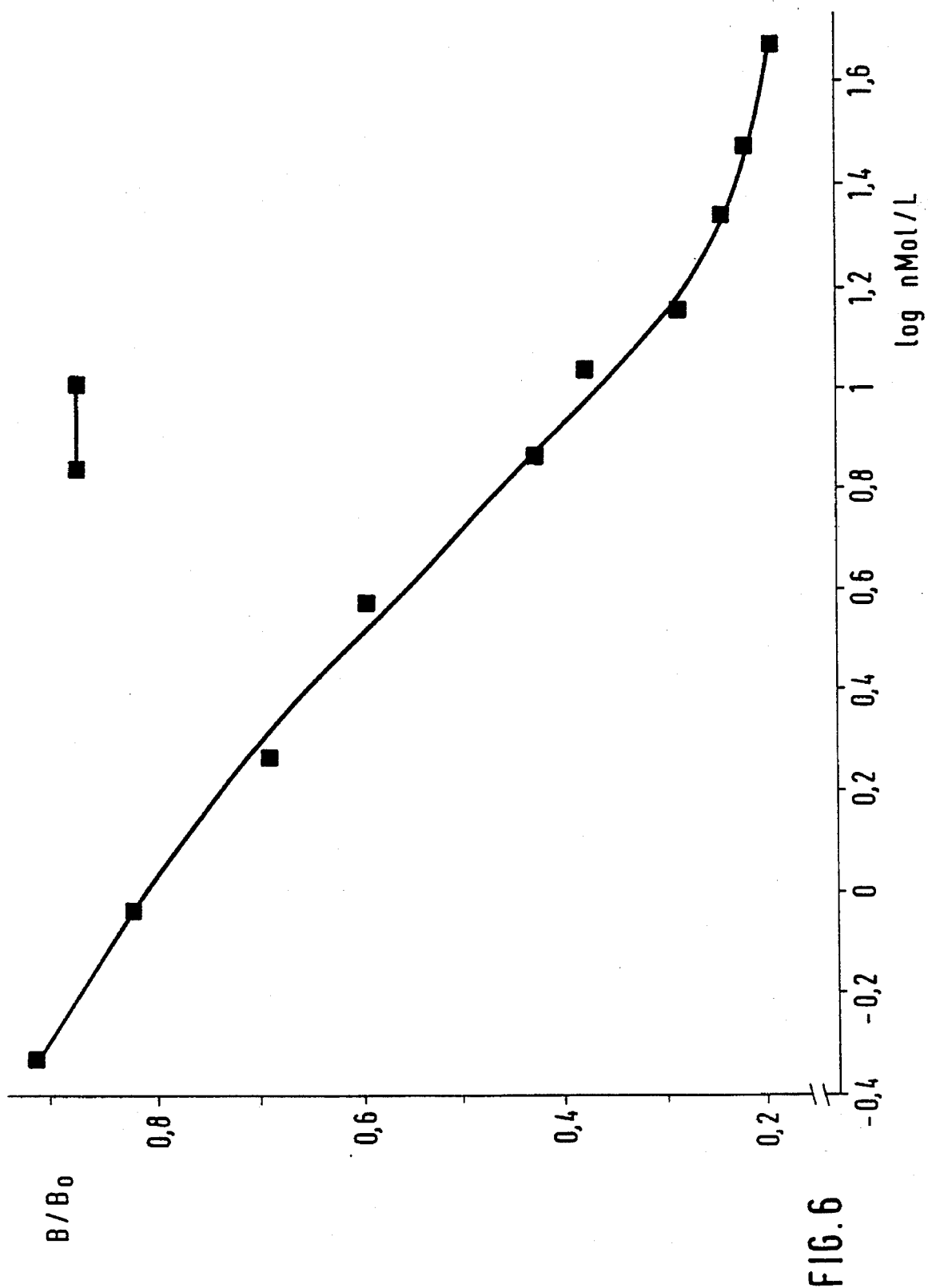
Figure 7:
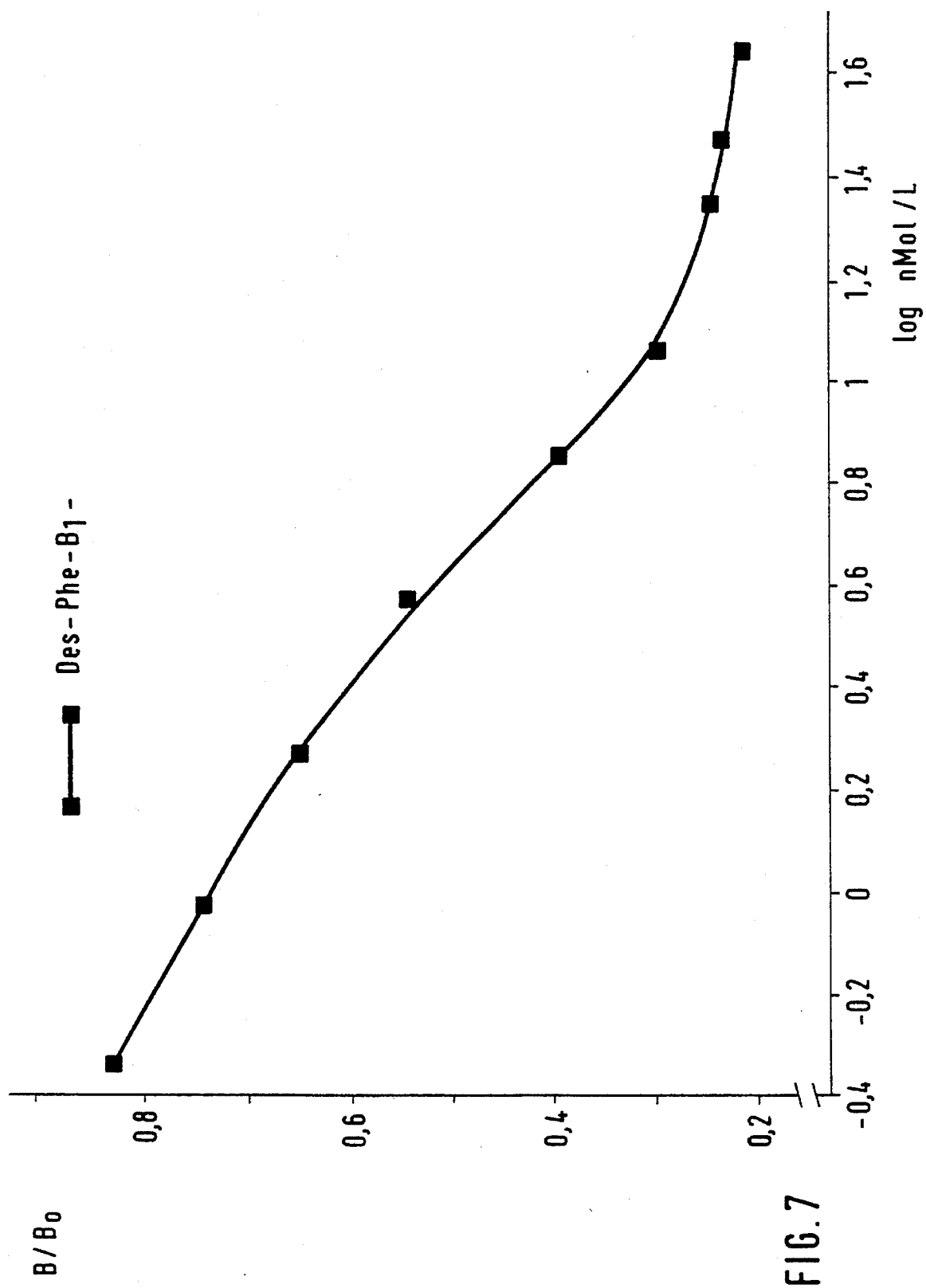
Figure 8:
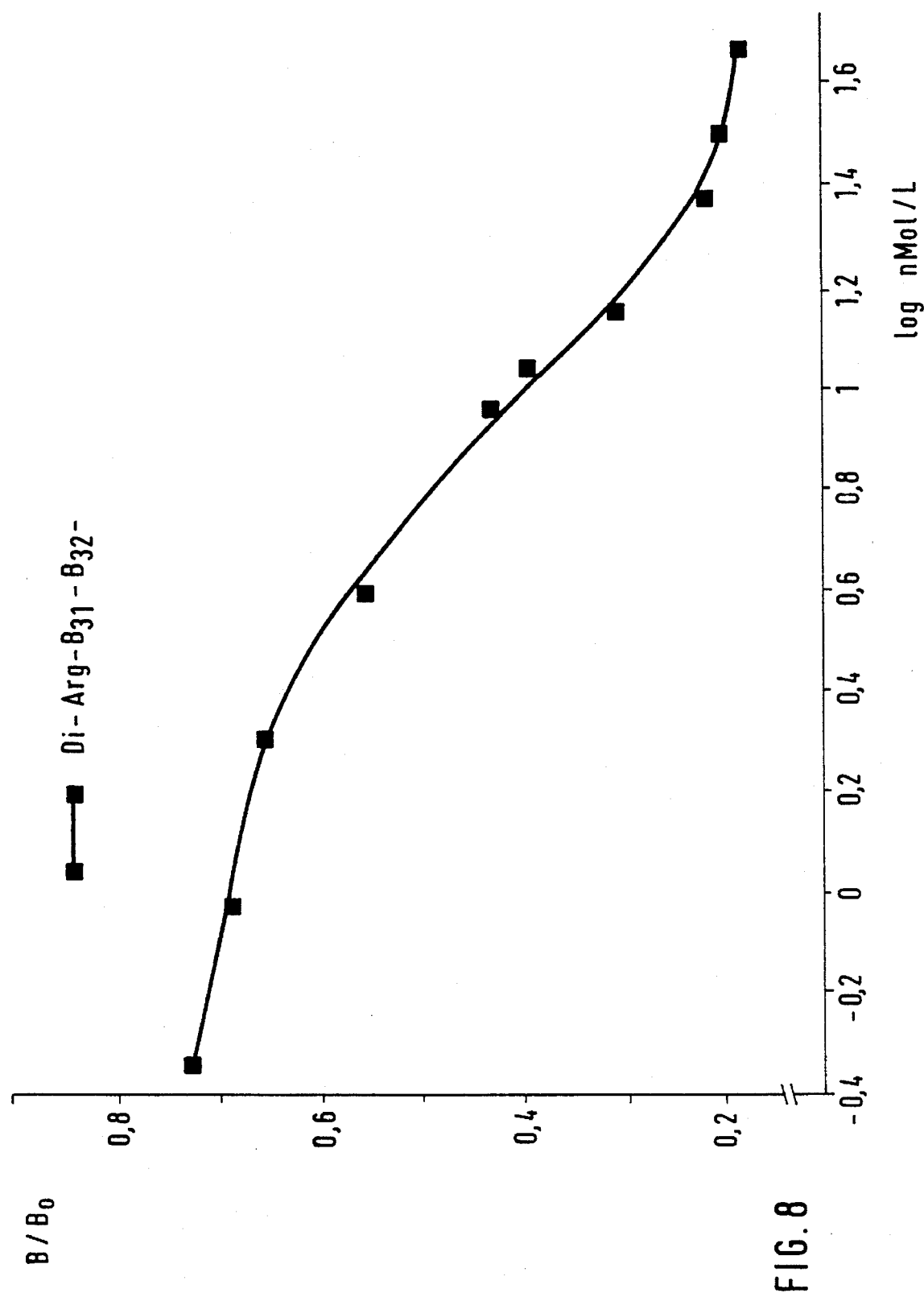
Figure 9:
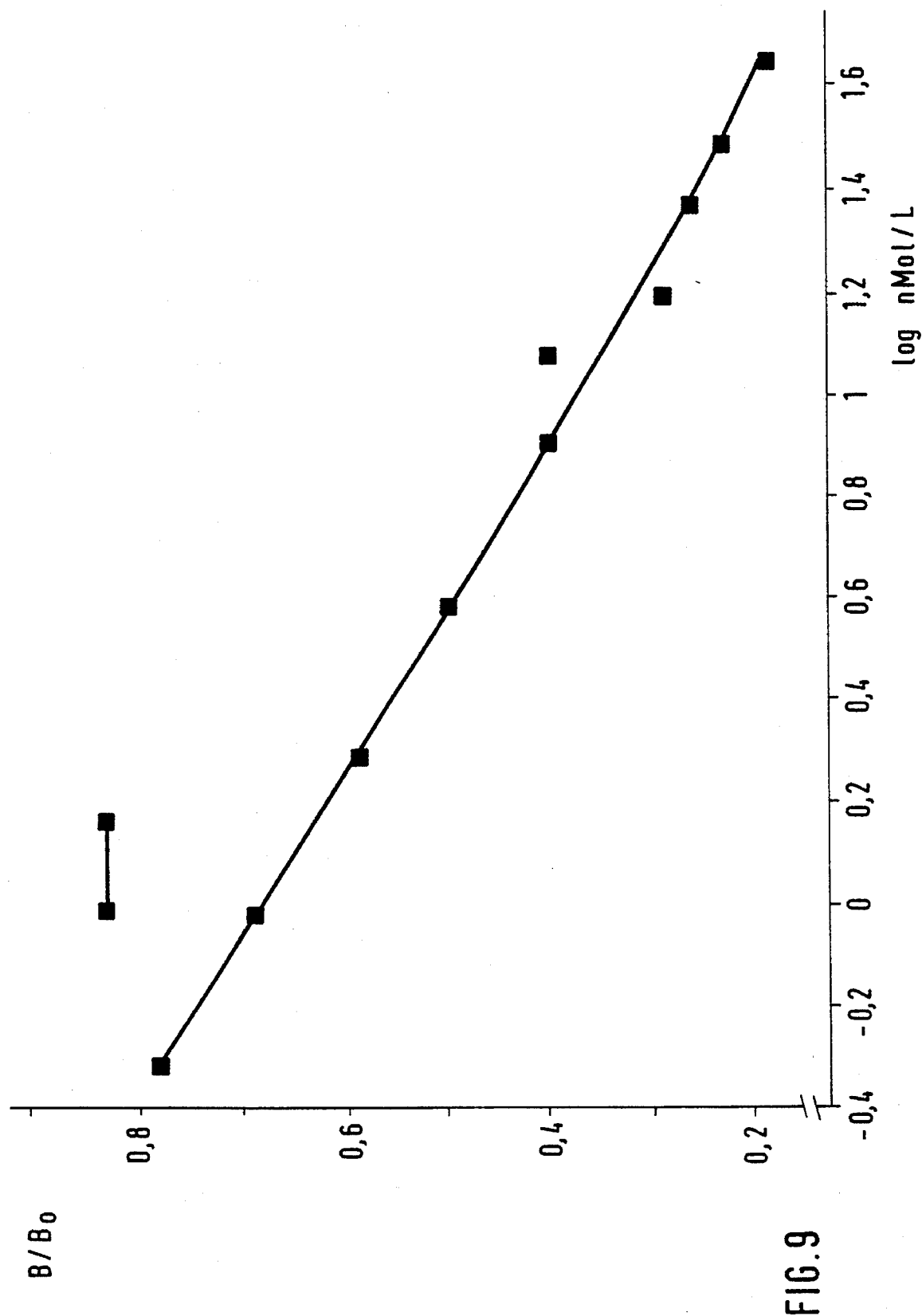
Figure 10:
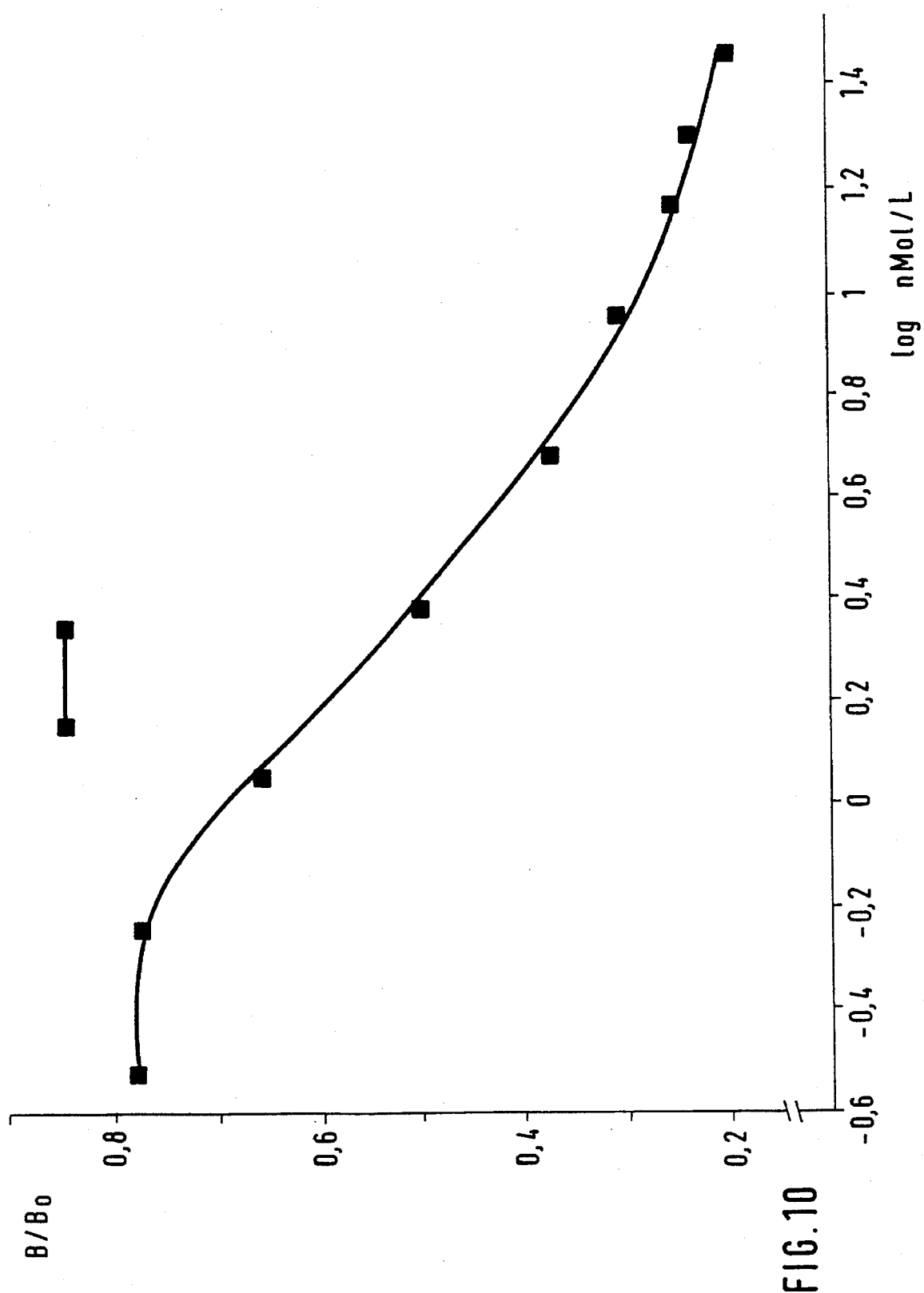
Figure 11:
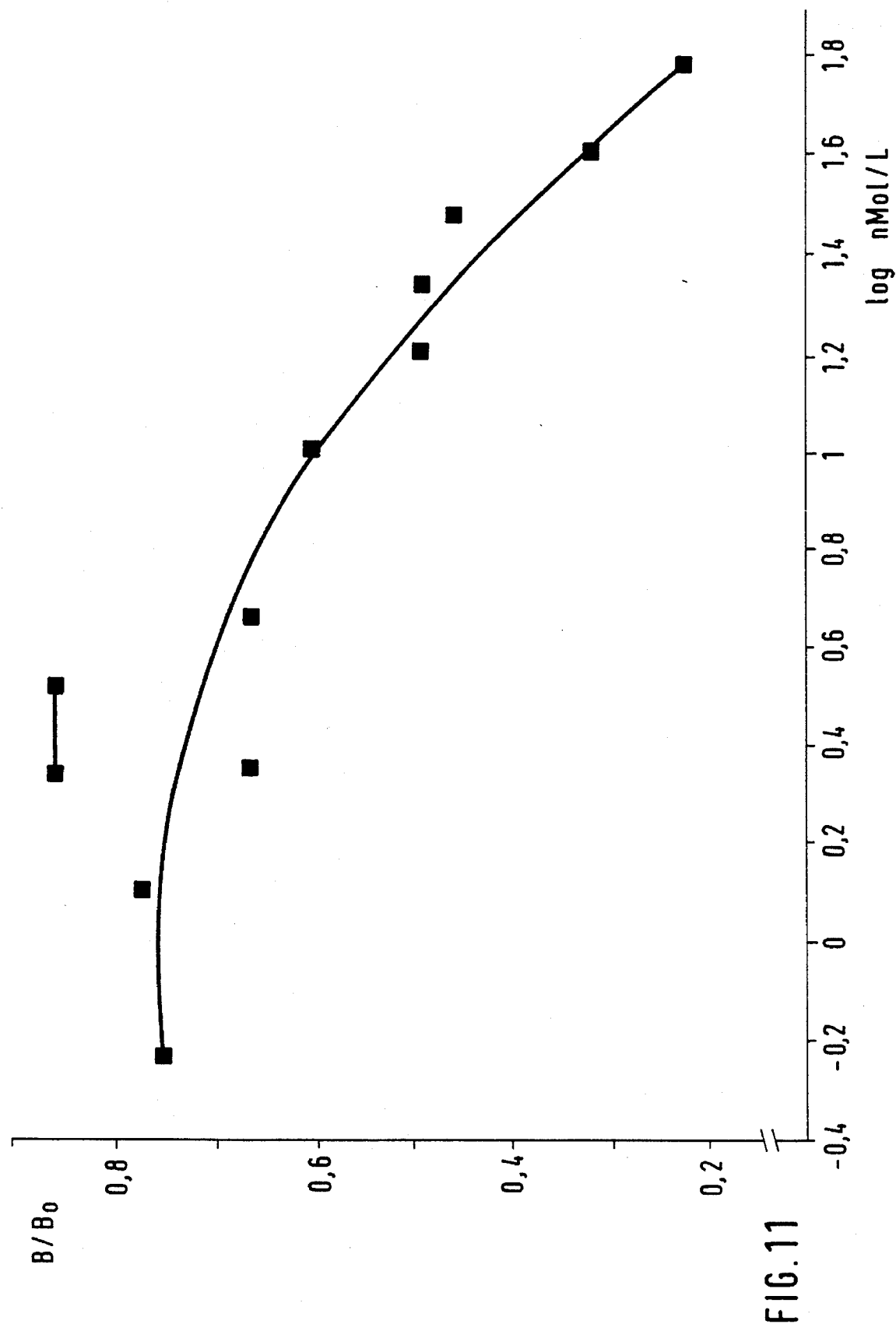
Figure 12:
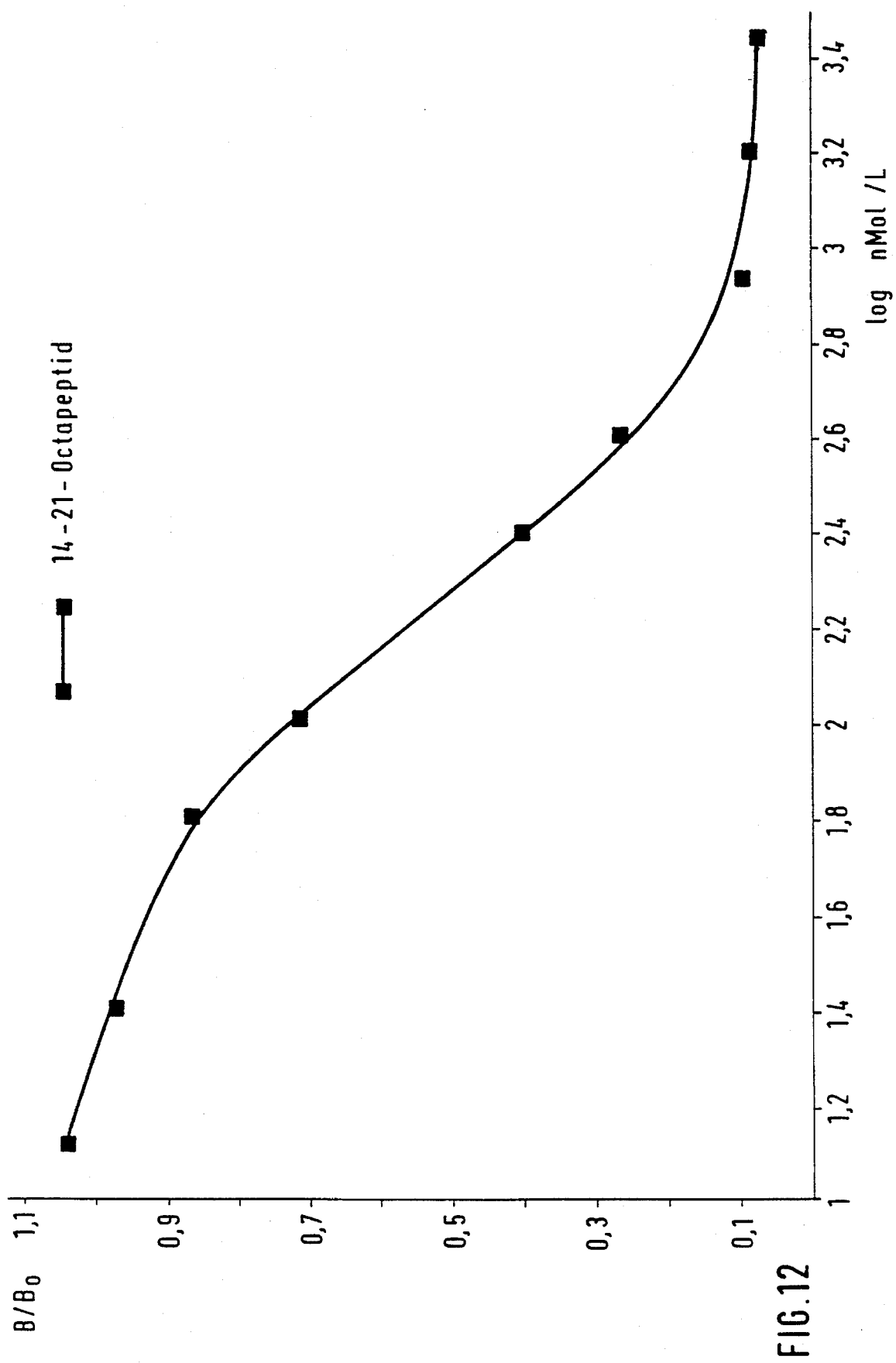
Figure 13:
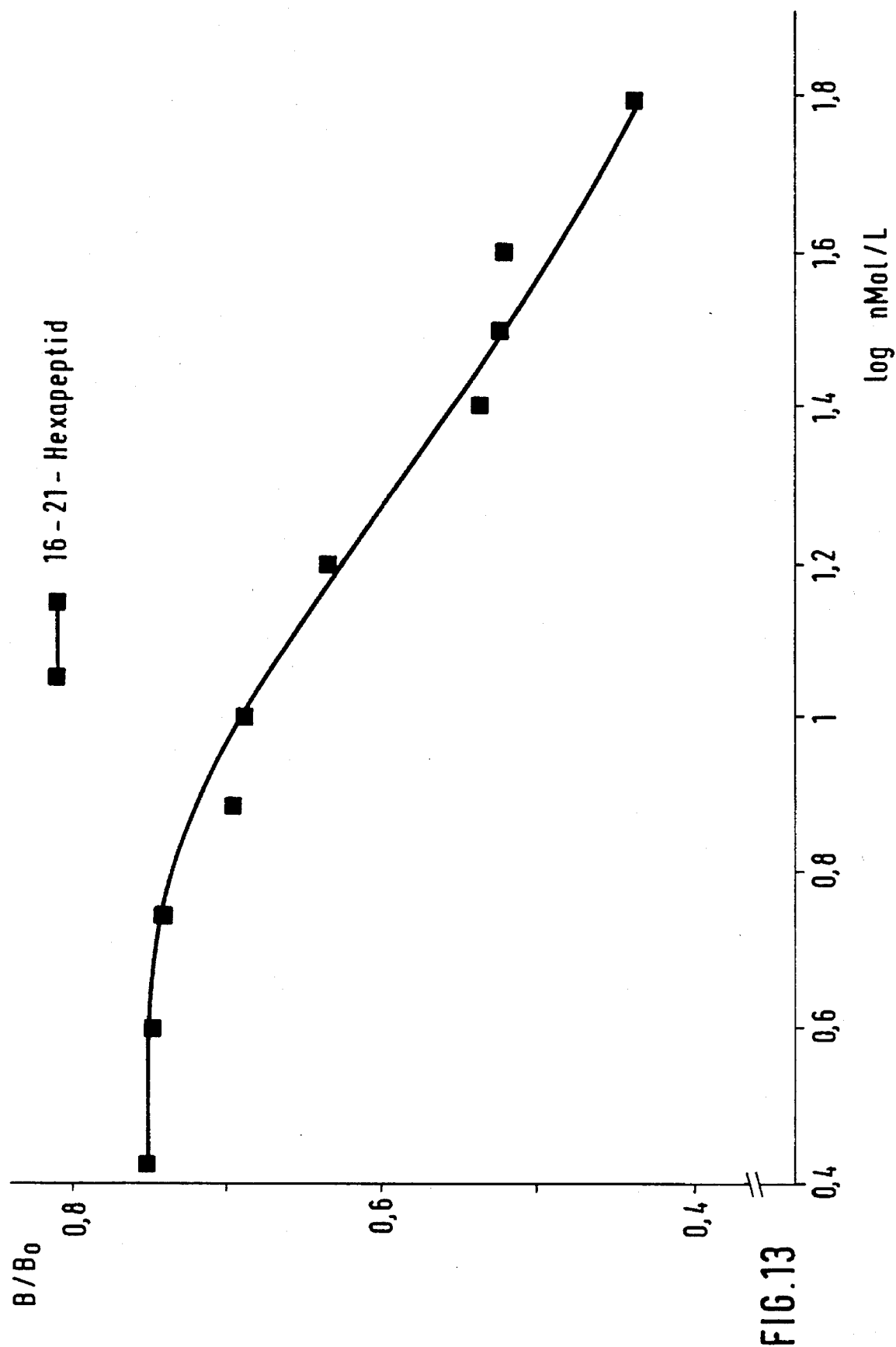

Based on the standard with a previously determined content of insulin or protein derived from insulin (see Example 3: Standards), standard plots were recorded for the following insulins: Human insulin (FIG. 1), pig insulin (FIG. 2), cattle insulin (FIG. 3), sheep insulin (FIG. 4), chicken insulin (FIG. 5) and horse insulin (FIG. 6), the derivatives de-Phe-B1-pig insulin (FIG. 7), di-Arg-B31-B32-human insulin (FIG. 8), mono-Arg-B31-human insulin (FIG. 9), pig proinsulin (FIG. 10) as well as insulin A chain tetrasulfonate (FIG. 11) and (14–21) octapeptide (FIG. 12) and (16–21) hexapeptide (FIG. 13).

The values $B/B_0$ stated in the figures indicate the quotient of the measured activity B and the maximum activity $B_0$ (complete saturation of the antibody with tracer). The standard plots shown in the FIGS. 1–13 clearly demonstrate that a sensitive detection method for a large number of insulins has been provided by the RIA according to the invention using the antibodies according to the invention.

Figure 14:
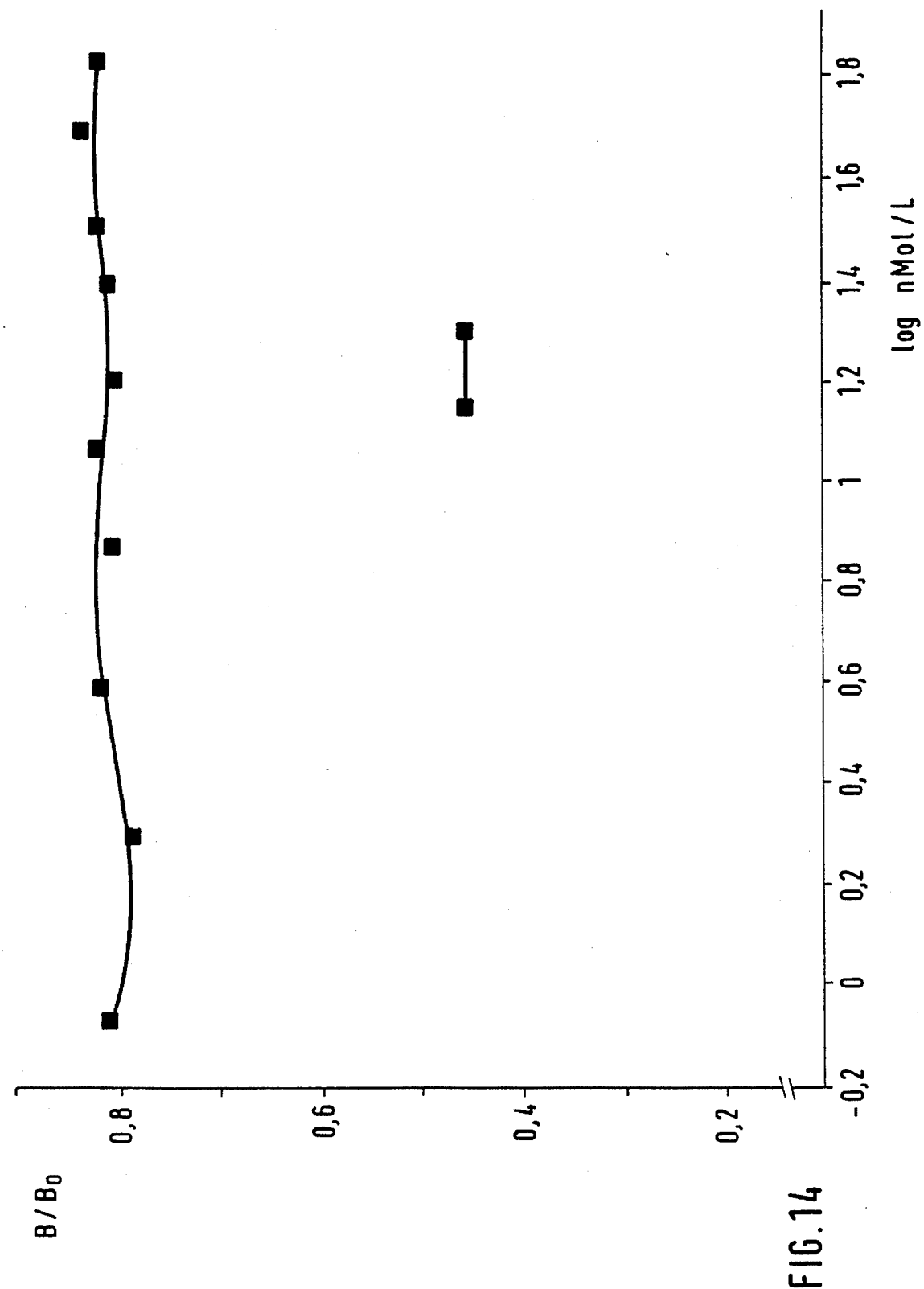
Figure 15:
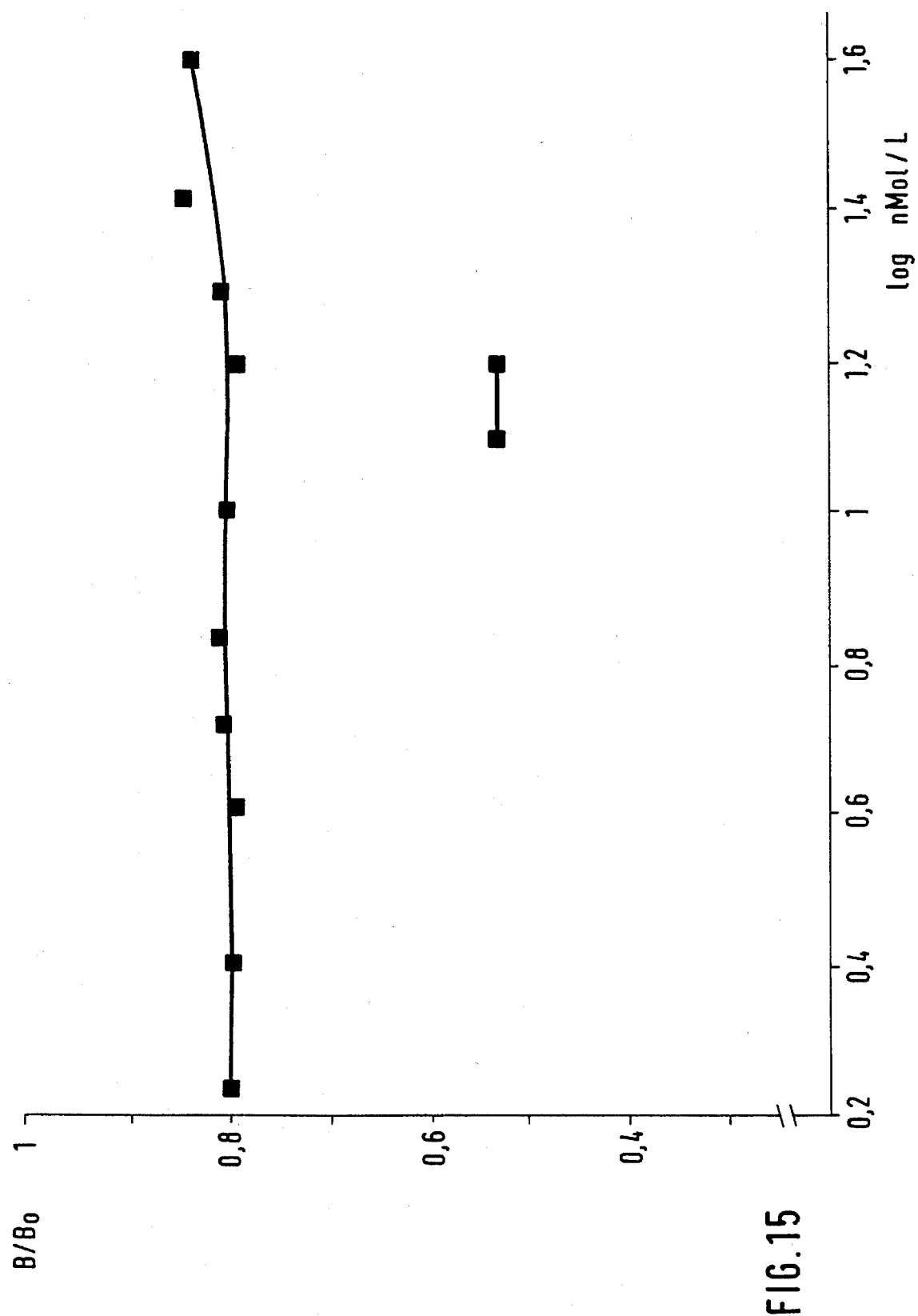

The influence of foreign proteins and of the buffer system on the measurements was investigated and it was found that high concentrations of neither BSA nor *E. coli* proteins result in any interference with the assay. Calcitonin and buserelin were added in the same concentrations as the octapeptide to the assay mixture as negative control in order to demonstrate the absence of cross-reactivity with small peptide structures. No cross-reactivity was found (see FIG. 14 and FIG. 15).

I claim:

1. An immunoassay method for the detection of an insulin or insulin derivative, comprising the steps of:
   (i) contacting said insulin or insulin derivative with one or more antibodies, wherein said antibody or antibodies are obtained by immunization with a peptide fragment selected from the group consisting of Tyr-Gln-Leu-Glu-Asn-Tyr-Cys-Asn and Leu-Glu-Asn-Tyr-Cys-Asn of the insulin A chain, and
   (ii) detecting the amount of said insulin or insulin derivative which binds to said antibody or antibodies.

2. The immunoassay as claimed in claim 1, wherein a labeled antigen which forms an immune complex with the antibody or antibodies is added in step (i).

3. The immunoassay as claimed in claim 1, wherein at least one antibody is labeled.

4. The immunoassay as claimed in claim 2, wherein labeling is carried out with a radioactive, a chemiluminescent or an enzymatic label.

5. The immunoassay as claimed in claim 1, wherein said antibody or antibodies are immobilized on a solid phase.

6. The immunoassay as claimed in claim 1, wherein step (i) and/or step (ii) are carried out in the presence of one or more detergents and/or one or more auxiliary proteins and/or one or more detergent/auxiliary protein mixtures.

7. The immunoassay as claimed in claim 6, wherein step (i) and/or step (ii) are carried out in the presence of at least one ionic and at least one nonionic detergent.

8. The immunoassay as claimed in claim 1, wherein at least one antibody of step (i) is a monoclonal antibody.

9. An immunoassay kit comprising one or more antibodies, wherein said antibody or antibodies are obtained by immunization with a peptide fragment selected from the group consisting of Tyr-Gln-Leu-Glu-Asn-Tyr-Cys-Asn and Leu-Glu-Asn-Tyr-Cys-Asn of the insulin A chain.

10. The immunoassay method of claim 1 wherein said peptide fragment is Leu-Glu-Asn-Tyr-Cys-Asn of the insulin A chain.

11. An immunoassay method as claimed in claim 1 wherein the amino acid sequence of said peptide fragment is Tyr-Gln-Leu-Glu-Asn-Tyr-Cys-Asn.

12. A method for measuring the insulin content of genetically engineered fusion proteins in inclusion bodies in microorganisms, comprising the steps of
   expressing said proteins in a microorganism; and
   detecting the amount of insulin by the method of claim 1.

13. A method for measuring the insulin content of genetically engineered fusion proteins in inclusion bodies in microorganisms, comprising the steps of
   expressing said proteins in a microorganism; and
   detecting the amount of insulin by the method of claim 7.

* * * * *